US00PP34010P3

(12) United States Plant Patent
Bodapati et al.

(10) Patent No.: US PP34,010 P3
(45) Date of Patent: Mar. 15, 2022

(54) ***PONGAMIA* TREE NAMED 'K206'**

(50) Latin Name: ***Pongamia pinnata* (L) Pierre**
Varietal Denomination: K206

(71) Applicant: TerViva, Inc., Oakland, CA (US)

(72) Inventors: Naidu Bodapati, Riverhills (AU); Marshall Mackay, Tewantin (AU); Naveen Sikka, Oakland, CA (US); David Harry, Philomath, OR (US)

(73) Assignee: Terviva, Inc., Oakland, CA (US)

( * ) Notice: Subject to any disclaimer, the term of this patent is extended or adjusted under 35 U.S.C. 154(b) by 0 days.

(21) Appl. No.: 16/602,150

(22) Filed: Aug. 14, 2019

(65) Prior Publication Data

US 2020/0068764 P1 Feb. 27, 2020

Related U.S. Application Data

(60) Provisional application No. 62/722,102, filed on Aug. 23, 2018.

(51) Int. Cl.
*A01H 5/00* (2018.01)
*A01H 6/54* (2018.01)

(52) U.S. Cl.
USPC ..... Plt./216
CPC ..... *A01H 6/54* (2018.05)

(58) Field of Classification Search
USPC ..... Plt./216
CPC ..... A01H 6/00; A01H 5/00; A01H 6/54
See application file for complete search history.

(56) References Cited

U.S. PATENT DOCUMENTS

PP26,060 P3 11/2015 Bodapati et al.
PP26,061 P3 11/2015 Bodapati et al.
PP26,062 P3 11/2015 Bodapati et al.

OTHER PUBLICATIONS

Biswas et al. (Int. J. Mol. Sci. 15: 7380-7397, 2014).*
Statement of claim filed in the Supreme Court of Queensland by Bioenergy Plantations Australia Pty Ltd. dated Oct. 9, 2020, 15 pages.

* cited by examiner

*Primary Examiner* — Keith O. Robinson
(74) *Attorney, Agent, or Firm* — Morrison & Foerster LLP

(57) ABSTRACT

A new and distinct variety of *Pongamia* tree (*Pongamia pinnata* (L) Pierre) named 'K206' is provided herein. *Pongamia* tree 'K206' is distinguished by having an open canopy, medium sized leaves with olive green color, short current season's twigs, long inflorescences, and abundant production of seed pods coupled with the high oil content of the seeds.

9 Drawing Sheets

Latin name: Botanical classification: *Pongamia pinnata* (L) Pierre.

Varietal denomination: The varietal denomination of the claimed variety of *Pongamia* tree is 'K206'.

BACKGROUND OF THE INVENTION

*Pongamia* is a species of tree that belongs to the Fabaceae family of plants. The botanical classification of *Pongamia* is *Pongamia pinnata* (L) Pierre, although these plants are also known by a number of synonymous botanical classifications including, for example, *Millettia pinnata* (L) Panigrahi, *Derris indica* (Lam.) Bennet, *Pongamia glabra* Vent, and *Cytisus pinnatus* (L).

As a member of the Fabaceae family of plants, *Pongamia* trees are legumes and are capable of fixing their own nitrogen. *Pongamia* can grow well in a variety of environmental conditions, including areas with malnourished soil. *Pongamia* seeds also contain a profile of chemicals having a number of uses including, for example, commercial preparation into skin ointment and as a fuel source.

*Pongamia* trees are capable of growing in otherwise challenging environmental conditions and produce seed oils with beneficial properties. There exists a need for *Pongamia* varieties that are stable, high yielding, and agronomically sound.

SUMMARY OF THE INVENTION

In order to meet these needs, the present disclosure is directed to an improved variety of *Pongamia* tree. In particular, the disclosure relates to a new and distinct variety of *Pongamia* tree (*Pongamia pinnata* (L) Pierre), which has been denominated as 'K206'.

*Pongamia* tree 'K206' was discovered growing in a cultivated area in southeastern Queensland, Australia, wherein it and neighboring trees are grown for shade and other landscape amenities. The parentage of this tree is unknown, as is typical for trees cultivated in landscape plantings of this type.

The original donor tree (and source of clonal material) of 'K206' was identified and selected primarily on the basis of its consistent production of large and abundant seed pods, coupled with the high oil content (38.4%, dry-weight basis) of its large seeds. This selected individual was assigned identity number 'K206'. Subsequently, branch cuttings were collected from the donor tree and rooted by treating the cuttings with the rooting hormone indolebutyric acid (IBA) using either an aqueous solution of IBA (500 ppm) or a commercially available rooting powder. Dehydration of the cuttings was avoided by placing them in moistened rooting medium within a humid enclosed chamber. Rooting success varies from one collection event to another, which is normal for cuttings from mature trees. Typically, 10% or more of the cuttings initiated root development within 3-4 weeks.

*Pongamia* tree 'K206' has been asexually reproduced via rooted cuttings in the Brisbane area of Queensland, Australia, as well as in Texas and Florida, U.S.A. In addition, shoots of 'K206' have also been grafted onto seedling rootstock using either a top-cleft graft or a side-veneer graft. These asexually propagated plants remain true-to-type, and show considerable resemblance among one another after accounting for variation in overall size of the propagated cuttings and seedling rootstocks.

*Pongamia* tree 'K206' is particularly and distinctly characterized by its open canopy, upright branchlets, short current season's branches bearing long inflorescences, and copious quantities of fruit pods containing seeds with high seed-oil content (38.4%, dry-weight basis). Pods tend to appear in dense clusters. 'K206' demonstrates excellent vigor, with casual observations suggesting it is reasonably resistant to insect and disease pests, at least relative to other *Pongamia* trees growing in the general vicinity. However, susceptibility or resistance to specific insect and disease pests has not been determined.

DESCRIPTION OF THE DRAWINGS

*Pongamia* tree 'K206' is illustrated by the accompanying photographs, which show e.g. the plant's form, branches, foliage, leaves, trunk, pods, and seeds as specifically described below. The colors shown are as true as can be reasonably obtained by conventional photographic procedures.

DETAILED BOTANICAL DESCRIPTION OF THE PLANT

Figure 1:
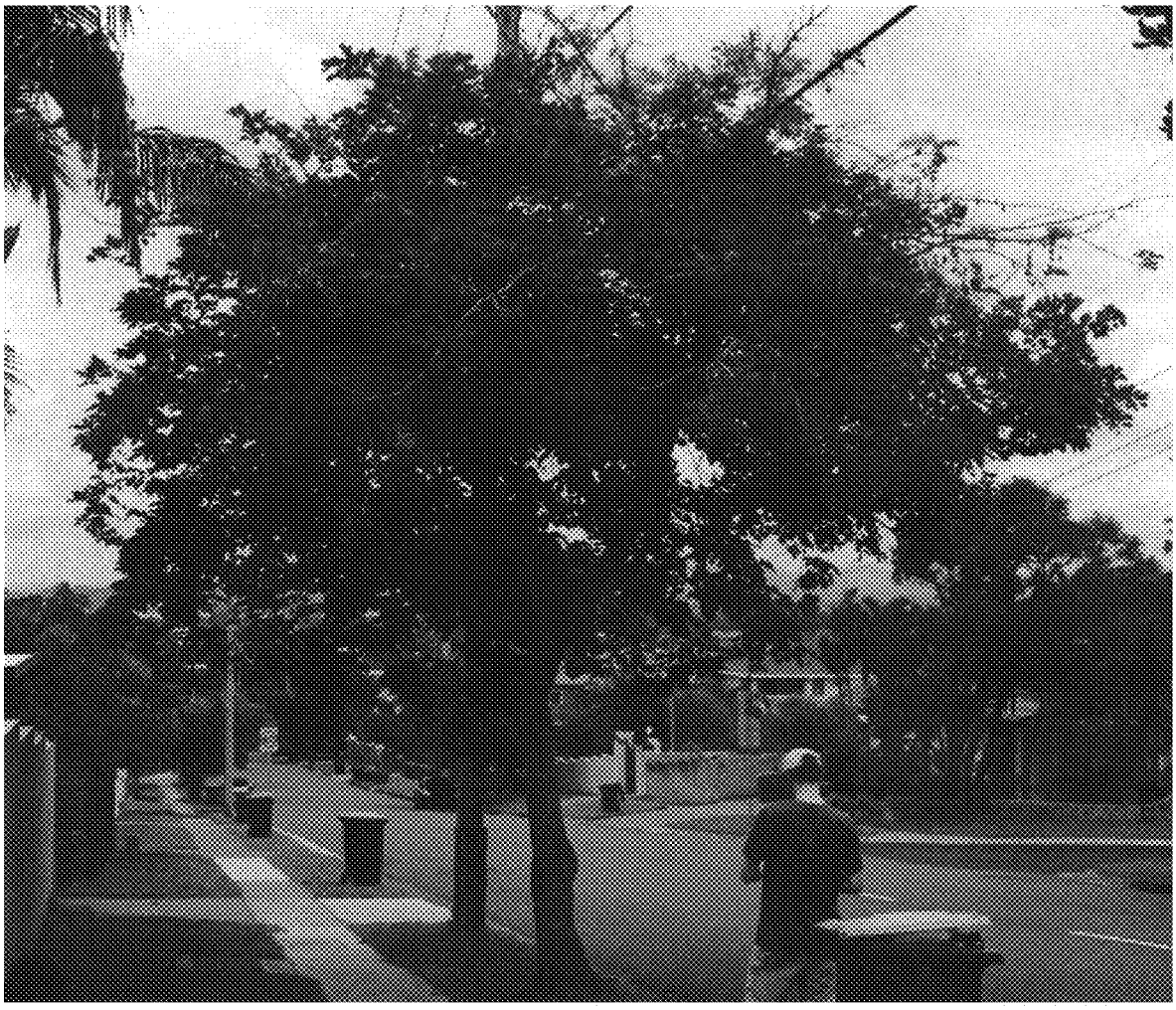
FIG. 1 illustrates a view of the whole tree of *Pongamia* tree 'K206' in Queensland, Australia. The depicted tree was estimated to be 15-20 years old when photographed.
Figure 2:
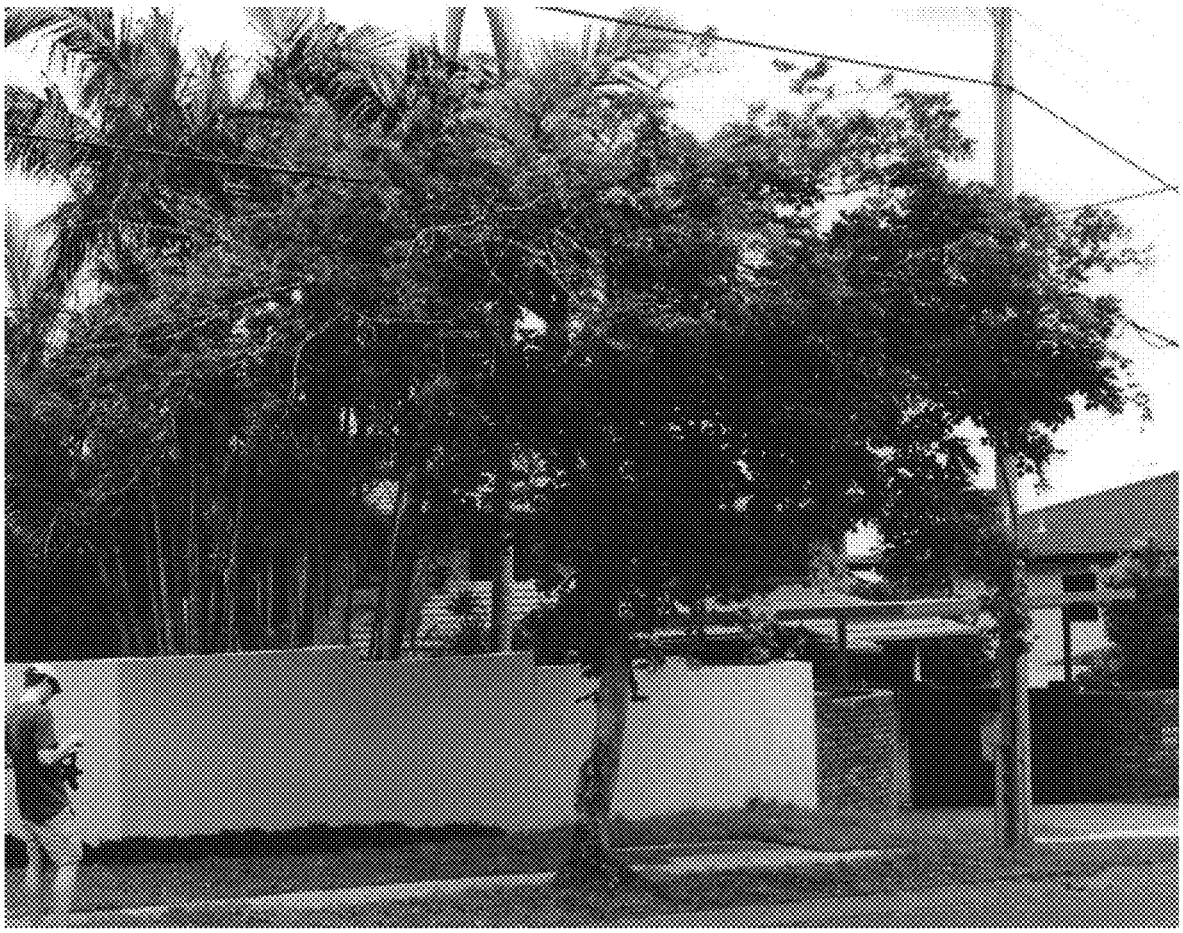
FIG. 2 illustrates a view of the whole tree of *Pongamia* tree 'K206' in Queensland, Australia. The depicted tree was estimated to be 15-20 years old when photographed.
Figure 3:
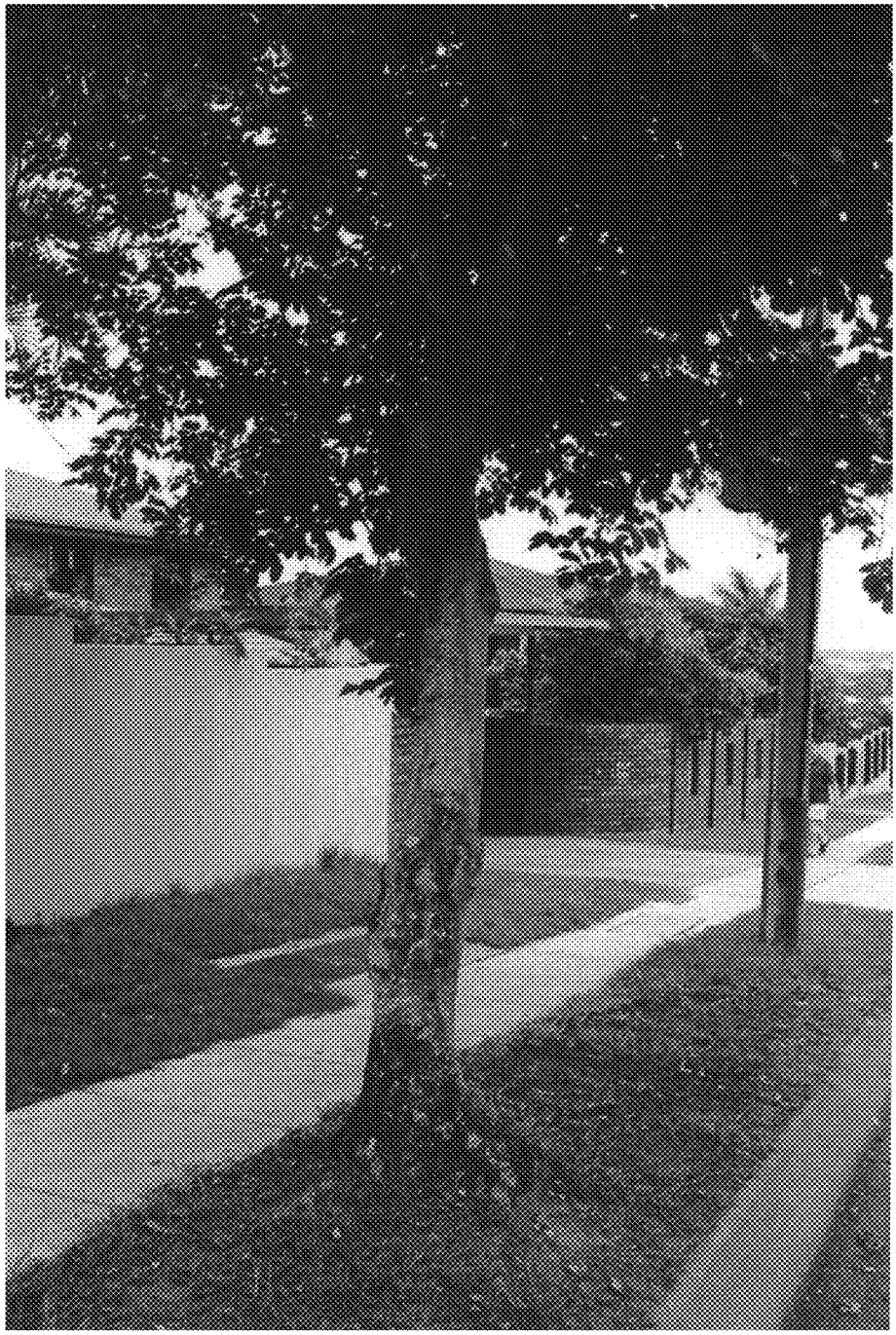
FIG. 3 illustrates a view of the tree trunk of *Pongamia* tree 'K206' in Queensland, Australia. The depicted tree was estimated to be 15-20 years old when photographed.
Figure 4:
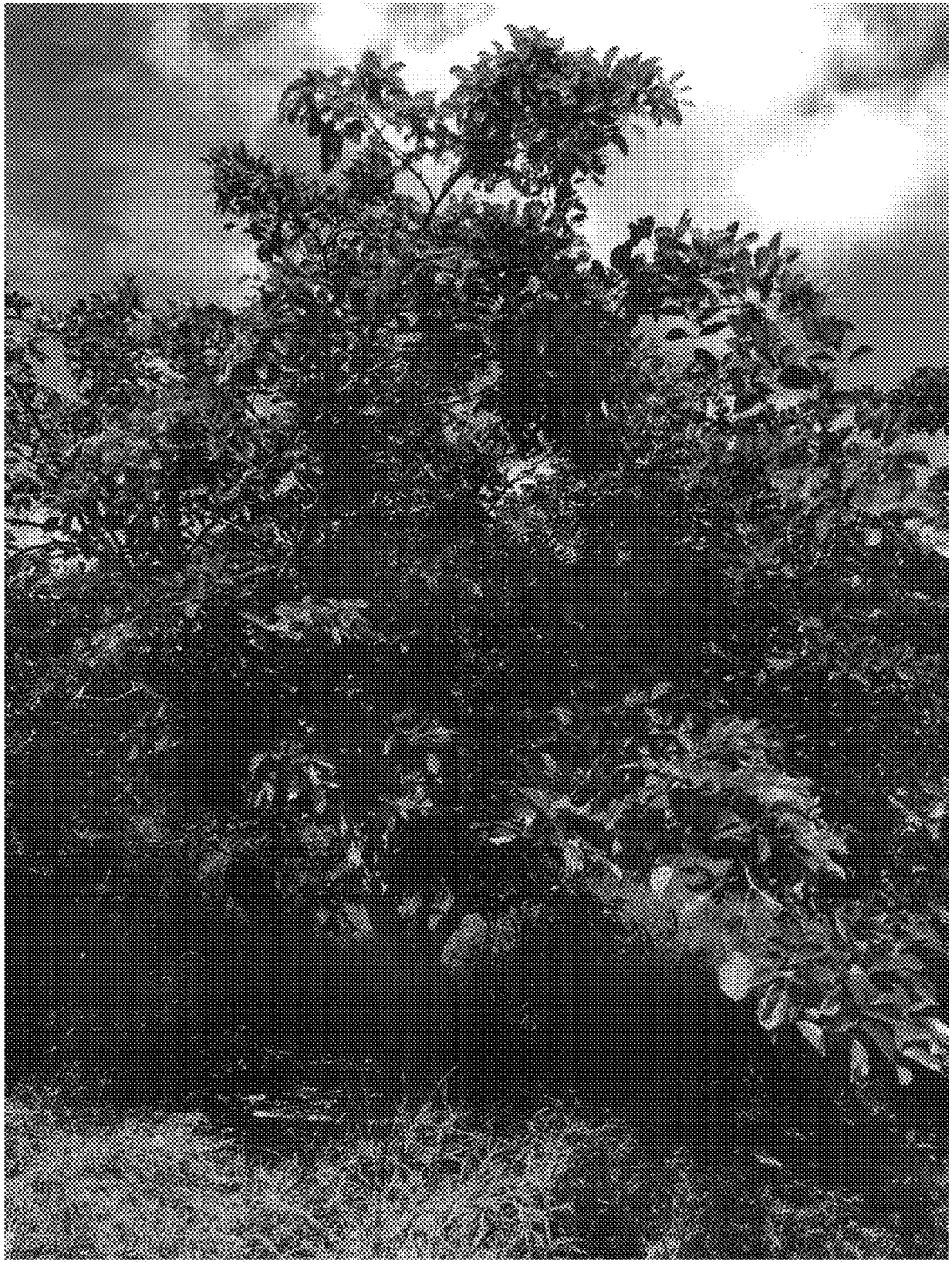
FIG. 4 illustrates a view of a 5-year-old clonally propagated 'K206' tree in Florida, USA.
Figure 5:
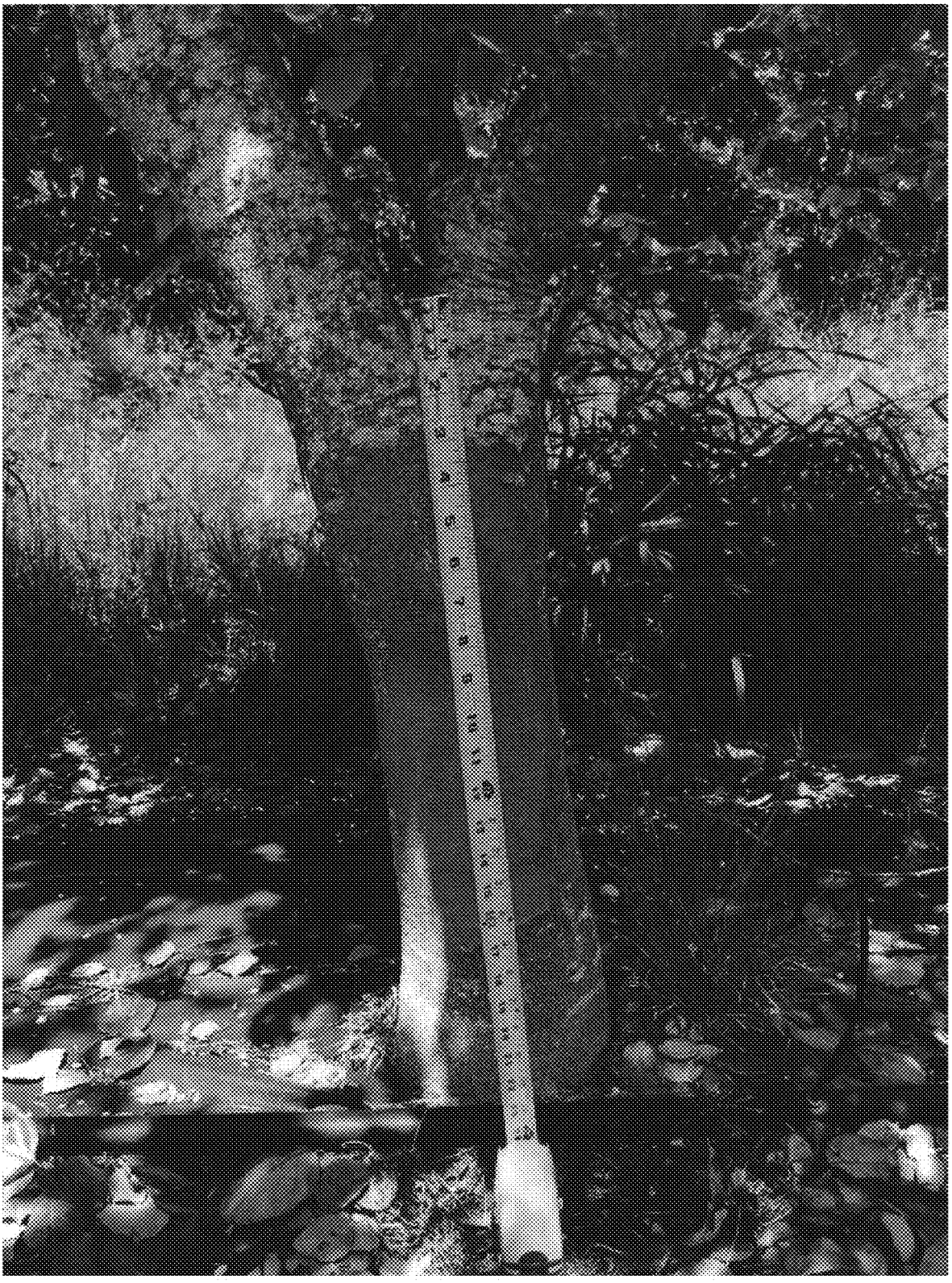
FIG. 5 illustrates a 5-year-old clonally propagated 'K206' tree in Florida with the smooth bark on the main trunk. Mottled patches on the bark primarily reflect differences in lichen growth. Stretched lenticular scars appear as horizontal striations along the bark.
Figure 6:
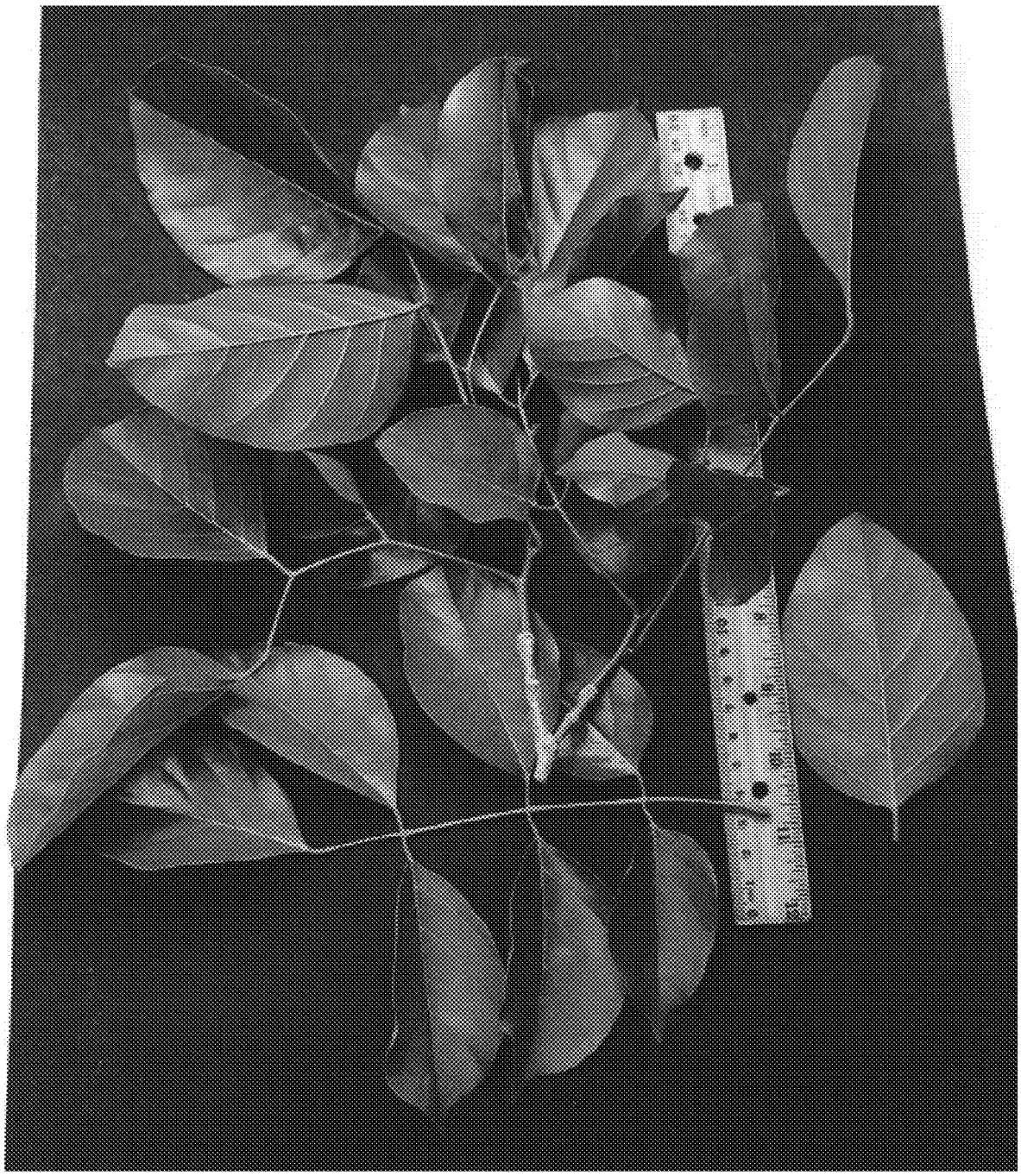
FIG. 6 illustrates the short current season's branchlets and odd-pinnately compound leaves from a 5-year-old clonally propagated Florida-grown 'K206' tree. The compound leaves generally have 7 leaflets. The leaflet at the bottom (right) is oriented to show the underside.
Figure 7:
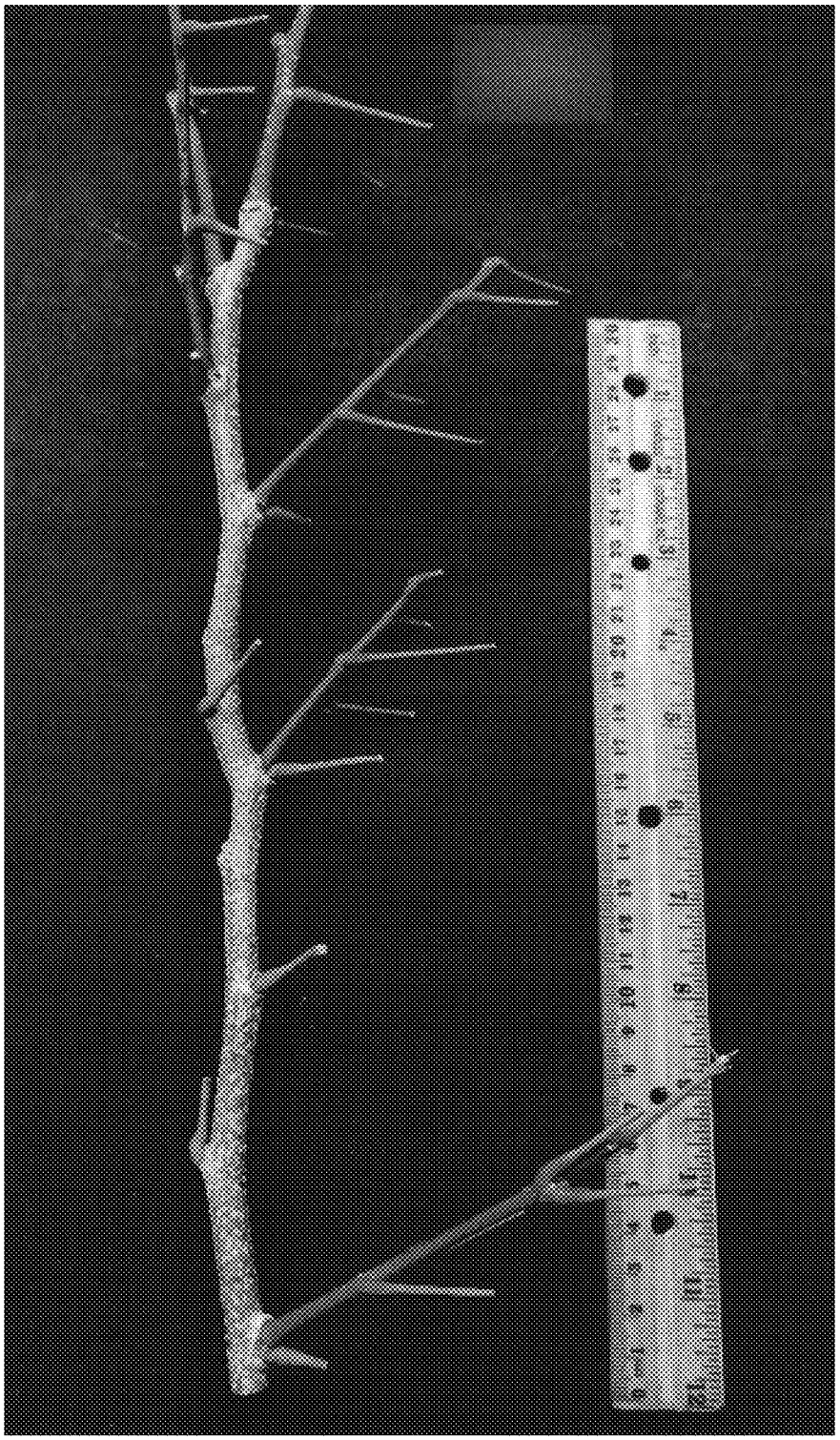
FIG. 7 illustrates the irregular branching pattern arising from the leaf axils and short current season's twigs from a 5-year-old clonally propagated Florida-grown 'K206' tree. Leaves were removed for clarity.
Figure 8:
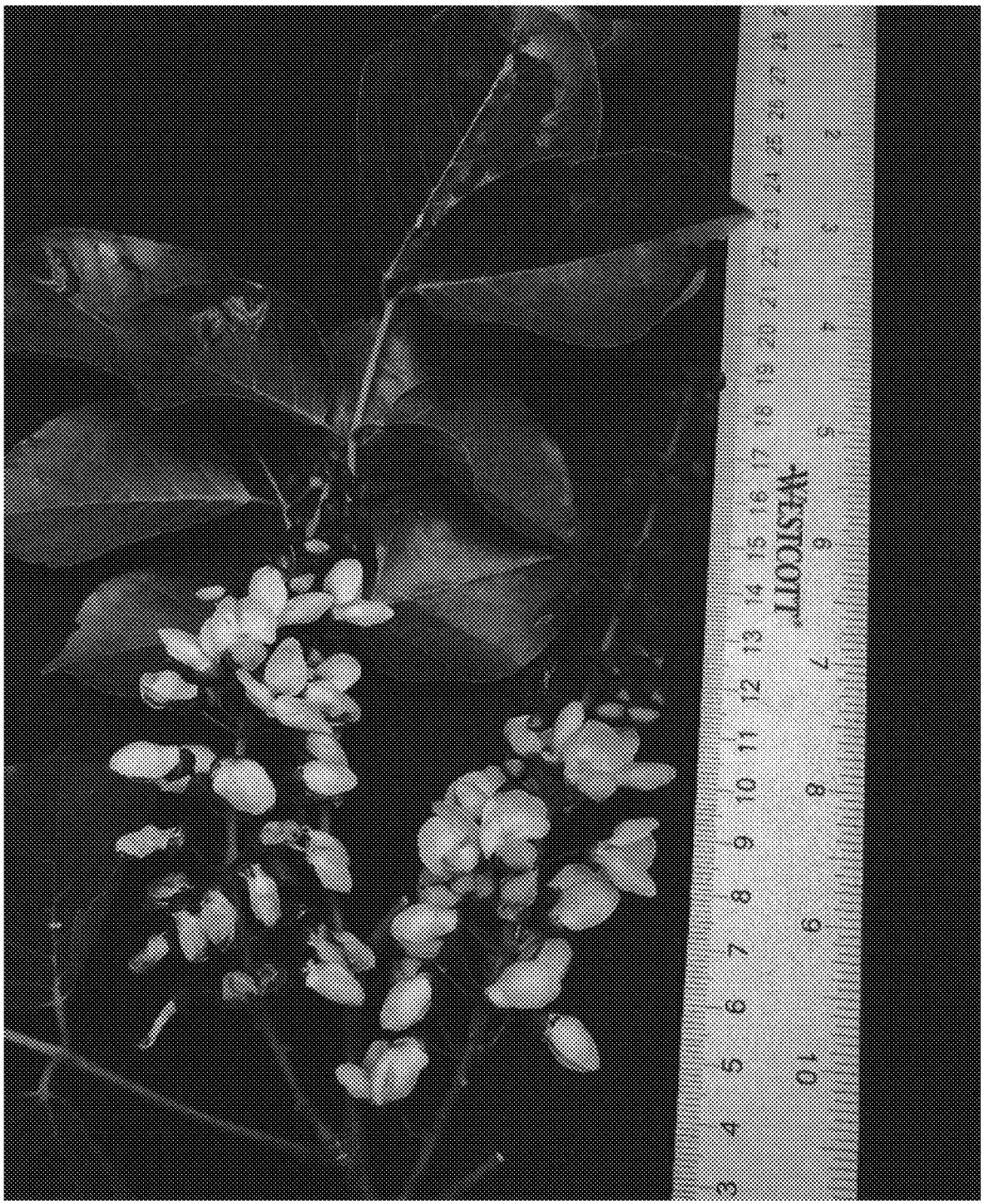
FIG. 8 illustrates the long inflorescences from a 5-year-old clonally propagated Florida-grown 'K206' tree.
Figure 9:
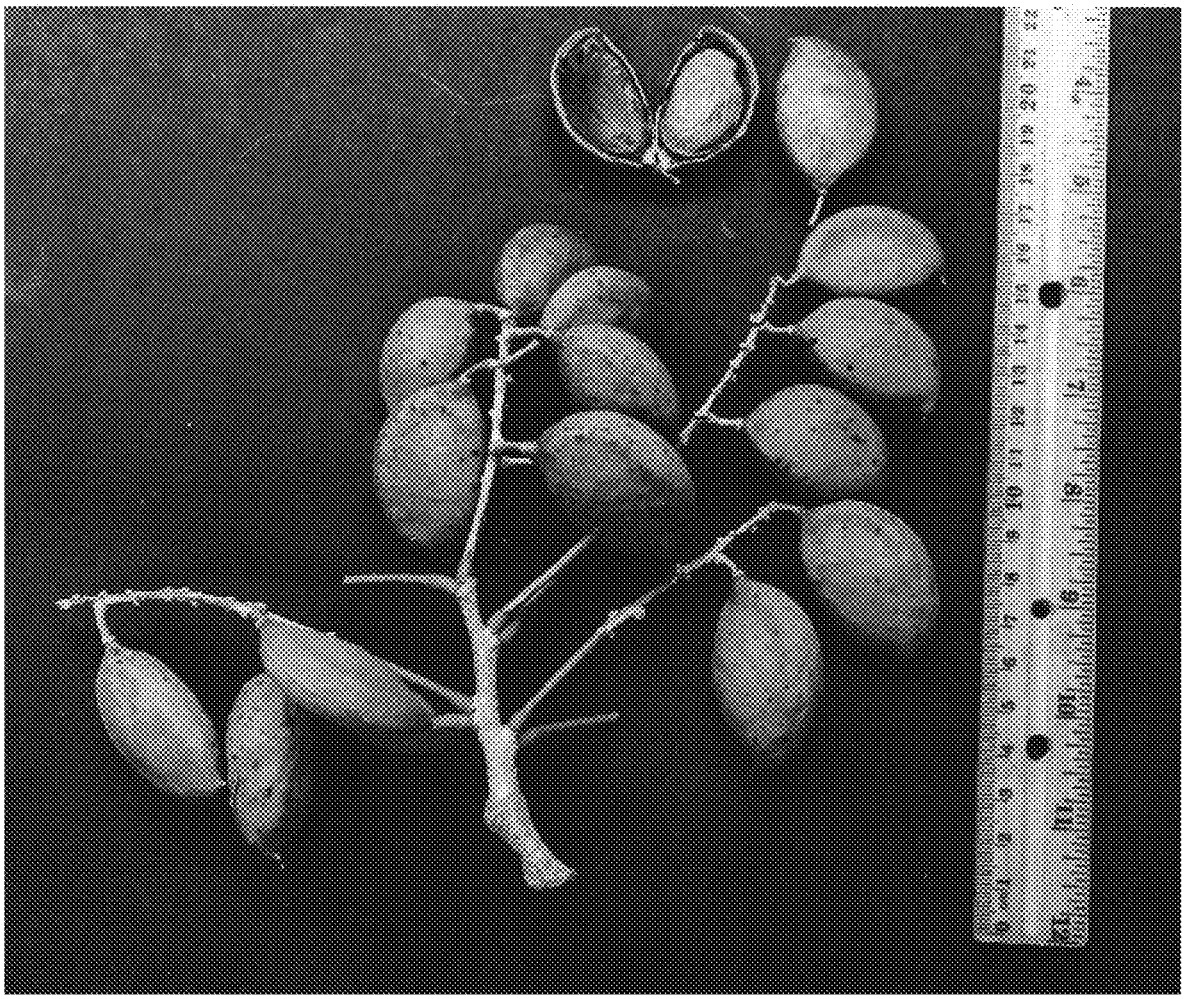
FIG. 9 illustrates semi-mature pods along with fully mature dry pods of a 5-year-old clonally propagated Florida-grown *Pongamia* tree 'K206'. Dry pods are split open to show seed. The branch shown has 4 rachises borne in the axils of basal leaves. Each rachis bears 3-6 immature pods. Leaves were removed for clarity.

The following detailed description sets forth the phenotypic characteristics and the distinctive features of *Pongamia* tree 'K206'. Descriptions are from trees that are 5 years post-transplant into the field in Florida, USA unless otherwise noted. Standardized color designations herein are with reference to The Royal Horticultural Society (R.H.S.) Mini Colour Chart, Sixth Edition, 2015.

Classification:

*Family.*—Fabaceae.

*Botanical.*—*Pongamia pinnata* (L) Pierre.

*Common name.*—Pongam tree, pongam oiltree, or *Pongamia.*

Tree:

*Size.*—Vigorous tree of moderate size and stature, 7 m in height. Crown diameter, measured at the drip-line in two dimensions, is 5 m×6 m.

*Trunk.*—The trunk of a 5-year-old Florida tree is bifurcated at a height of 60 cm from the ground, with the average breast-height diameter of these two major stems measuring 9 cm. The trunk can have numerous epicormic branches at its base, however, this trait is somewhat variable among different trees. On 5-year-old trees in Florida, epicormic branches numbered 0-4 along 61 cm of basil trunk, averaging 3. The fresh vegetative growth on an epicormic shoot ranges from 15 cm to 50 cm long and from about 3.5 mm to 8.0 mm in diameter.

*Bark.*—Light olive grey in color (RHS 197B) with smooth or faintly vertically fissured bark on the main trunk. Light-colored greyish yellow green (RHS 197D) and dark-colored greyish yellow green (RHS 198A) mottled patches on the bark reflect differences in lichen growth.

*Form.*—Decurrent crown form with younger open-grown trees having greater breadth than height. Average height of five four-year-old trees in Florida was 3.0 m (range of 2.2 to 3.4 m) whereas their average crown width was 6.1 m (range of 5.8 to 6.6 m). The canopy is characterized by open foilage and upright outer branchlets. Periodic pruning may be used for size maintenance.

Branches

*Branch numbers and dimensions.*—Primary branches from the main stem are stout. On a 5-year-old tree in Florida, the average breast-height diameter of two major branches (bifurcated from the main trunk at 60 cm above the ground) is 9 cm. Height of primary branching often reflects management activities because a clear basal stem is preferred. In a second Florida field, with 4-year-old trees, 3 primary branches occur at approximately 80-90 cm above the ground, and average 6.3 cm in diameter (range 5.6 to 7.2 cm). The bark color of these primary branches closely resembles the color of the main trunk (greyish yellow green, RHS 196A).

*Branching habit.*—Many smaller branches occur on the periphery of the crown, but are too numerous to count. These peripheral branches result in a semi-dense canopy (e.g. in comparison to *Pongamia* variety 'K207' (U.S. Plant patent application Ser. No. 16/602,152)) that arises, in part, from a reduced tendency (relative to 'K207') of axillary buds to elongate into axillary shoots along year-old shoots (i.e. wood from the previous year). Averaged over three branches on each of three trees, the outermost meter of year-old stem encompassed 19.3 nodes, with on average only one elongating to form an axillary shoot.

*Buds and shoots.*—Young shoots emerge from naked lateral buds, with the most distal bud (a false terminal bud) giving rise to a terminal shoot. Buds are hemispherical and range from 2.5 mm to 4.5 mm wide at their base. Buds protrude outward 1.5 mm to 3.0 mm from the stem and are between 1.0 mm to 1.5 mm thick. The typical axillary bud is strong yellow green in color (RHS 143A), and the younger terminal bud is strong yellow green in color (RHS 144A).

*Terminal shoots.*—The seasonal elongation of terminal shoots on main branches is moderate, with an average of 20 cm and encompassing 7 leaf nodes. The average stem diameter of terminal shoots is 12.5 mm.

*Lateral shoots.*—Seasonal elongation of lateral shoots is considerably short, with an average length of 20 cm and bearing 6 leaf nodes. The average diameter of lateral shoots is 3.5 mm.

*Shoot and twig surfaces.*—Woody twigs have leaf scars that are 3.5 mm to 4.0 mm wide, showing traces of three vascular bundles. The central scar tends to have a border that is less distinct than the outer two. Stipule scars are pale orange yellow (RHS 159C). The youngest shoots are hairless and distinctly strong yellow green in color (RHS 143A) and flexible, with no lenticels apparent to the naked eye. As shoots mature, their color shifts to light greyish olive (RHS 195A) and prominent lenticels become visible as raised, light yellow-colored (RHS 162C) corky circles approximately 1.5 mm in diameter.

Leaves:

*General.*—Alternate, imparipinnate with long slender leafstalk, and hairless. Most leaves show 7 leaflets.

*Size and shape.*—The outline of a compound leaf is roughly oval to elliptic, with an average length of 25 cm and an average width of 15 cm.

*Leaflets.*—Blades of individual leaflets are ovate to cordate in shape with a cuspidate to mucronate apex. Leaflet venation tends to be arcuate. Blades of terminal leaflets have an average length of 8 cm and an average width of 6 cm. The smallest leaflet on a leaf tends to be a basal leaflet with an average length of 7 cm and an average width of 5 cm.

*Leaflet color, surface, and texture.*—Leaflets are glabrous on both abaxial and adaxial surfaces. Young leaves exhibit a strikingly glossy cuticle on their adaxial surface. The adaxial (upper) and abaxial surface of a young leaflet is strong yellow green in color (RHS 144A). The adaxial surface of an old leaf is moderate olive green in color (RHS 137A), and the abaxial surface of an older leaflet is moderate hellow green in color (RHS 137C) with prominent veins beneath. The color changes described above accompany the gradual maturation of younder to older leaves (and leaflets), occurring over several (3-5) weeks, depending on the season. As they mature, leaves and leaflets also become increasingly sclerophyllous.

*Stipules.*—A pair of small stipules subtends the youngest leaves on a shoot. Stipules are strong yellow green (RHS 144B) and are approximately 10 mm long by 3 mm wide, with a glabrous surface and entire margins. Stipules remain for only a short duration before they dehisce.

Flowers and inflorescences:

*General.*—Hermaphroditic florets are borne on an indeterminate inflorescence.

*Inflorescence structure.*—Several florets are clustered into a fascicle node, which are generally evenly distributed along a rachis. The entire inflorescence is a pseudoraceme. Most inflorescences are unbranched, but some are branched.

*Position in crown.*—'K206' has relatively long inflorescences with an average length of 19 cm. There are an average of 4 inflorescences per lateral shoot. Inflorescences are borne in the basal leaf axils of the current year's vegetative flush, near the distal end of the prior year's shoot growth. Each rachis may hold an average of 95 florets.

*Florets.*—Emerge acropetally from a fused ovoid calyx with entire margins and glabrous texture. The calyx has an average depth of 4.0 mm and width of 4.5 mm, and is greyish red in color (RHS 176A) on both the inner and outer surfaces. The average length of pedicles is 7.0 mm and the average diameter is 0.5 mm. Pedicels can be dark purple (RHS 83A). Zygomorphic florets consist of 2 keel, 2 wing, and a standard (or banner) petal, and have a depth of 12.1 mm and a diameter of 10.5 mm. The banner petal is very light purple in color (RHS 75C) towards the edges; and has a strong yellow green (RHS 144A) streak in the middle. The banner petal's apex shows a notch, and the base is rounded. Wing petals are typically 7.7 mm long and the exposed part is moderate purplish pink in color (RHS N74D). The two keel petals are fused together enclosing the stamens and pistil, it is white in color (RHS NN155B), and the distal edges display moderate yellow color (RHS 161A). The 10 stamens are fused and enclose the pistil.

*Flowering period.*—Relative to other *Pongamia* cultivars in the general area, 'K206' tends to flower about mid-range into the flowering period (from November to December in southeastern Queensland, Australia; and early-mid June in Florida, USA).

Fruits:

*General.*—Only one of the two ovules develop into a seed in most of the pods. Immediately after fertilization, the peduncular ovule usually aborts and remains as a small unfilled seed. Only the stigmatic ovule develops into seed, thus pods usually bear a single seed.

*Shape and color.*—Developing fruits first appear as moderate yellow green (RHS 146C) flattened pods, expanding in size into a moderate orange yellow (RHS 164B) woody appearance when pods mature.

*Crown distribution*.—Pods can occur throughout the crown, but are most prevalent towards the outer portions of the crown.

*Fruit clusters*.—Pods within a cluster are connected by the rachis of the inflorescence from which they developed, with an average of 8 pods/bunch.

*Pod dimensions*.—Average length of the pod is 33.6 mm, average width of the pod is 18.2 mm, and average thickness of the pod is 9.5 mm. Pods range in shape from oval to half-moon, with an acuminate tip, and average 3.5 g in weight.

Seeds:

*General*.—Typically borne singly in pods. Sometimes an aborted (and much smaller) seed occurs alongside a fully-formed seed. About 1-5% of the pods may have two seeds.

*Seed coat*.—Seeds are covered by a thin seed coat that is usually moderate orange yellow in color (RHS 165C) when matured.

*Seed size*.—Average seed length is 22.3 mm, average seed width is 13.6 mm, and average seed thickness is 5.8 mm. Average seed weight is 1.9 g.

*Seed oil*.—Oil content is 38.4% oil on a dry-weight basis, which is higher than many other *Pongamia* cultivars.

*Nut crop*.—Mostly a regular bearer (generally in 2 of 3 years).

*Crop frequency*.—Most *Pongamia* cultivars rarely produce abundant nut crops consistently across multiple years. 'K206' bears pods more regularly than many other cultivars, generally producing a heavier crop in 2 out of 3 years, and a somewhat lighter crop in the third year.

*Ripening*.—Fruit ripening begins in late October and extends into December in southeast Queensland, Australia, and from June-July in Florida, USA. If undisturbed, pods remain in the crown for several weeks after they ripen.

COMPARISON WITH SIMILAR VARIETIES

Unlike *Pongamia* cultivars 'K128b (U.S. Plant Pat. No. 26,062), 'K140' (U.S. Plant Pat. No. 26,060), and 'K606' (U.S. Plant Pat. No. 26,061), 'K206' has a tendency to produce higher yields of pods in about 2 of 3 years, with pod yields in the third year being somewhat less. This pattern of pod yield tends to resemble the yield pattern of cultivar 'K207' (U.S. Plant patent application Ser. No. 16/602,152), although not necessarily during coincident years.

Seed oil content of 'K206', at 38.4% (dry-weight basis), is similar to that of 'K128b' (38.5%) and 'K606' (38.6%), and is less than that of 'K207' (40.6%) and 'K140' (41.4%).

Inflorescences of 'K206' are long and generally contain large numbers of florets (averaging 95) as compared to cultivars 'K128b', 'K140', 'K606', and 'K207'.

'K206' is similar to 'K606' in showing more vertically (upright) oriented branchlets than semi-pendulous branchlets (as found in 'K128b' and 'K207') and very pendulous branchlets (as found in 'K140'). This gives trees a more open canopy and allows more sunlight to reach leaves in the more interior portions of the canopy.

On 'K206' trees, relatively few axillary buds elongate and develop into current season's branchlets. This contrasts with 'K207', which shows very regular branches emerging from most of the auxillary buds. This may be related to the tendency of 'K206' to have a relatively open canopy.

Leaves on 'K206' trees usually contain 7 leaflets, and in that sense resemble cultivars 'K128b' and 'K140'. This contrasts with cultivar 'K207', in which leaves include a mixture of 5 or 7 leaflets.

We claim:

1. A new and distinct variety of *Pongamia pinnata* (L) Pierre tree named 'K206' as illustrated and described herein.

* * * * *